(12) United States Patent
Tong

(10) Patent No.: US 6,726,695 B2
(45) Date of Patent: Apr. 27, 2004

(54) FOUR-SPIKES SURGICAL SKIN STAPLE

(76) Inventor: Kun-Yuan Tong, 2308 W. Doublegate Dr., Albany, GA (US) 31707

( * ) Notice: Subject to any disclaimer, the term of this patent is extended or adjusted under 35 U.S.C. 154(b) by 575 days.

(21) Appl. No.: 09/810,094

(22) Filed: Mar. 19, 2001

(65) Prior Publication Data

US 2002/0133181 A1 Sep. 19, 2002

(51) Int. Cl.[7] .............................................. A61B 17/08
(52) U.S. Cl. ....................................... 606/151; 606/213
(58) Field of Search ................................ 606/213, 219, 606/221, 75; 411/457; 227/175.1

(56) References Cited

U.S. PATENT DOCUMENTS 4,467,805 A * 8/1984 Fukuda ................... 128/334 C
4,610,251 A * 9/1986 Kumst .................... 128/334 R

* cited by examiner

*Primary Examiner*—Henry Bennett
*Assistant Examiner*—Nihir B Patel

(57) ABSTRACT

A four-spikes surgical skin staple is composed of two stems which form a 60 degree angle V-shaped figure and four spikes, which are composed of two identical outer long spikes and two identical inner short spikes. Each of the two identical outer long spikes is fixed at a 60 degree angle to the outer end of each stem and each of the two identical inner short spikes is fixed at a 60 degree angle to the middle of each stem. The two outer long spikes are used to approximate the surgical incision wound and the two inner short spikes are used to stabilize the incision skin edges to prevent the overlapping of the skin edges. With no overlapping of the incision skin edges, the surgical incision wound can heal better and faster.

5 Claims, 2 Drawing Sheets

FOUR-SPIKES SURGICAL SKIN STAPLE

THE BACKGROUND OF THE INVENTION

The regular surgical skin staple has two spikes and turns around easily on the operative wound skin, because it has only one spike at each end and becomes rectangular shaped after it has been stapled onto the skin of the operative wound. When the surgical skin staple turns around in operative wound skin, the operative wound skin edges overlap each other and can not heal well. The new invented four-spikes surgical skin staple has two spikes on each end and can prevent the turning-around in the operative wound skin after it has been stapled onto the operative wound skin. Therefore, the four-spikes surgical skin staple can keep the operative wound skin well stabilized and prevent the overlapping of the operative wound skin.

THE BRIEF DESCRIPTION OF THE INVENTION

The four-spikes surgical skin staple has two spikes on each end. After being stapled onto the operative wound skin, the four-spikes surgical skin staple has two spikes at each side to pin each side of operative wound skin to keep the skin surface well stabilized to prevent the overlapping of the operative wound skin. The outer two spikes of the four-spikes surgical skin staple can approximate the operative wound skin and the inner two spikes can stabilize skin edges to prevent them from overlapping each other.

THE DETAILED DESCRIPTION OF THE DRAWINGS

THE DETAILED DESCRIPTION OF THE INVENTION

Figure 1:
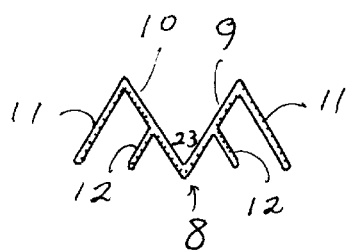
FIG. 1 is a perspective view of a four-spikes surgical skin staple before it is stapled onto the operative wound skin.
Figure 2:
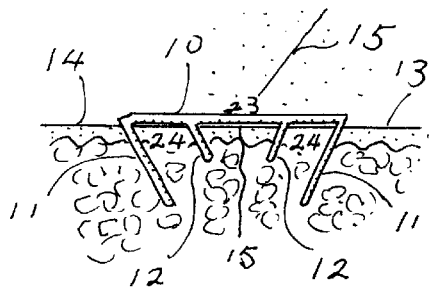
FIG. 2 is a perspective view of a four-spikes surgical skin staple after it has been stapled onto the the skin of the operative wound.
Figure 3:
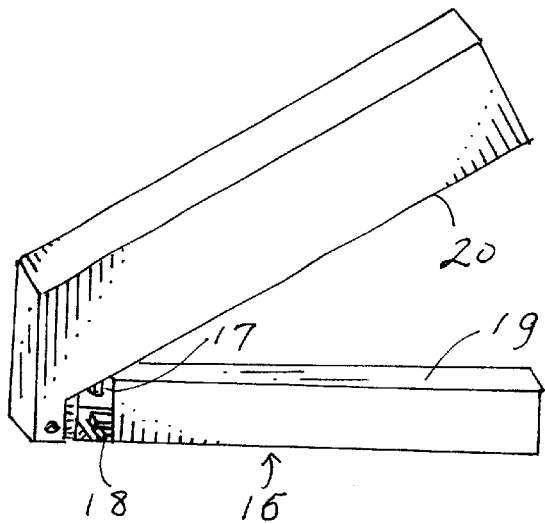
FIG. 3 is a perspective view of the applicator of a four-spikes surgical staple.
Figure 4:
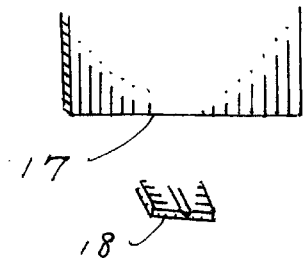
FIG. 4 is a perspective view of the stabilizer and the compressor of the applicator of a four-spikes surgical skin staple.
Figure 5:
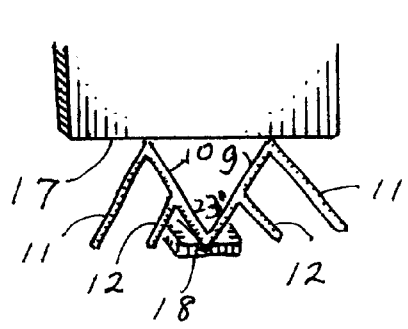
FIG. 5 is a perspective view of a four-spikes surgical skin staple loaded into the space between the stabilizer and compressor of the applicator of a four-spikes surgical skin staple.
Figure 6:
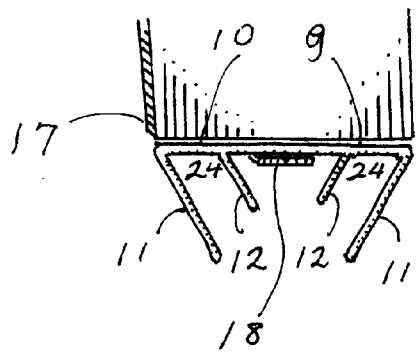
FIG. 6 is a perspective view of a four-spikes surgical skin staple after being compressed by the stabilizer and compressor of the applicator of four-spikes surgical skin staple.
Figure 7:
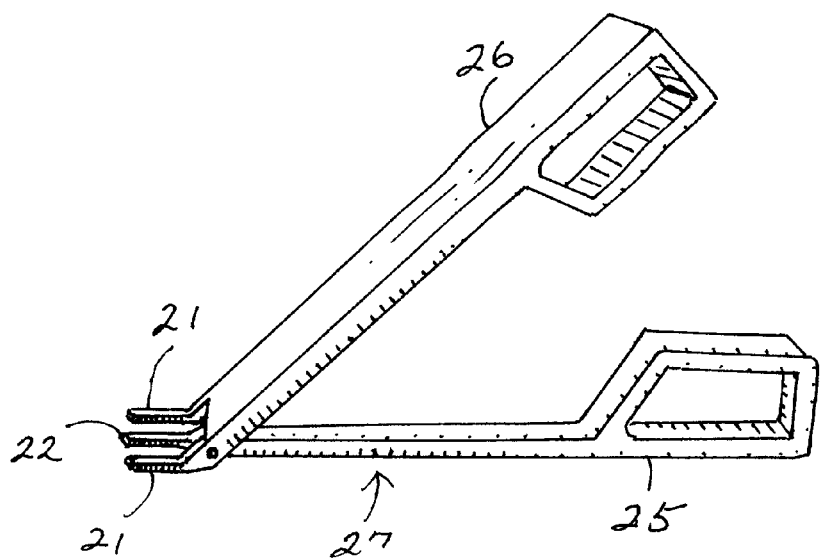
FIG. 7 is a perspective view of a four-spikes surgical skin staple remover.

Referring now in detail to the drawings, numeral 8 of FIG. 1 illustrates a four-spikes surgical skin staple which has two identical stems, 9 and 10. Each stem, 9 and 10, of FIG. 1 has an identical outer long spike 11 and an identical inner short spike 12. The spikes 11 and 12 are stapled onto each side of skin 13 and 14 to close the incision wound 15 as illustrated in FIG. 2. The applicator 16 of a four-spikes surgical skin staple 8 of FIG. 3 is equipped with a staple compressor 17, a staple stabilizer 18, a staple storage compartment 19 and a handle 20, as illustrated in FIG. 3. The arrangement of the staple compressor 17 and the staple stabilizer 18 is illustrated in FIG. 4. The arrangement of a four-spikes surgical skin staple 8 to the staple stabilizer 18 and the staple compressor 17 is illustrated in FIG. 5. After a four-spikes surgical skin staple 8 is compressed by the staple compressor 17 and the staple stabilizer 18, the stems 9 and 10 becomes flattened, as illustrated in FIG. 6. A staple remover 27 has two identical forks 21 and a central fork 22, as illustrated in FIG. 7. The two identical forks 21 are to be inserted into the spaces 24 between spikes 11 and 12 and the central fork 22 is to be placed on the top central point 23 of stems 9 and 10 before the two arms, 25 and 26, of the staple remover 27 are pressed together to remove a four-spikes surgical skin staple 8.

What is claimed is:

1. A four-spikes surgical skin staple composing of two identical stems which form a 60 degree angle V-shaped figure and four spikes which are divided equally and fixed at a 60 degree angle inward to the middle and outer end of each stem wherein said four spikes are arranged in two sets of identical spikes which are composed of one set of identical outer long spikes and one set of identical inner short spikes.

2. The staple compressor in claim 1 is a rectangular steel plate which has a width equal to that of the four-spikes surgical skin staple and a length which is equal to the sum of the length of the two identical stems and is used to compress the said four-spikes surgical skin staple.

3. The staple stabilizer in claim 1 is used to hold the four-spikes surgical skin staple when the staple compressor compresses on die four-spikes surgical skin staple.

4. The handle in claim 1 is used to push down the staple compressor.

5. The said handle in claim 2 is used to push down the said staple compressor in claim 3.

* * * * *